US00PP34843P2

(12) United States Plant Patent
Heuger

(10) Patent No.: US PP34,843 P2
(45) Date of Patent: Dec. 13, 2022

(54) ***HELLEBORUS* PLANT NAMED 'HL 1012'**

(50) Latin Name: ***Helleborus* x *lemperii (Helleborus niger* X *Helleborus* x *hybridus)***
Varietal Denomination: HL 1012

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 17/863,120

(22) Filed: Jul. 12, 2022

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'HL 1012', characterized by its upright to somewhat outwardly spreading and mounded plant habit; moderately vigorous to vigorous growth habit; dark green-colored leaves; freely flowering habit; reddish purple to light purple-colored flowers; and good garden performance.

2 Drawing Sheets

Figure 1:
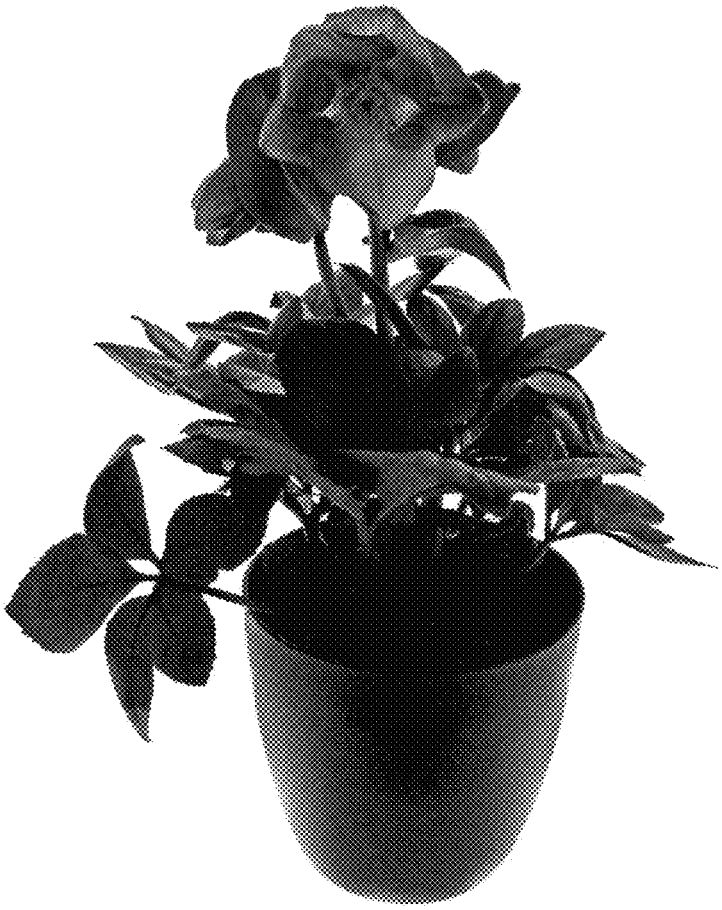

Botanical designation: *Helleborus* x *lemperii* (*Helleborus niger* X *Helleborus* x *hybridus*).
Cultivar denomination: 'HL 1012'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Nov. 30, 2021, application number 2021/3089. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *lemperii* (*Helleborus niger* X *Helleborus* x *hybridus*) and hereinafter referred to by the name 'HL 1012'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2012 of a proprietary selection of *Helleborus* x *lemperii* identified as code number 2013-0843, not patented, as the female, or seed, parent and a proprietary selection of

*Helleborus* x *lemperii* identified as code number 2012-0684, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by in vitro axillary meristem culture in a controlled environment in Glandorf, Germany since April, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1012'. These characteristics in combination distinguish 'HL 1012' as a new and distinct *Helleborus* plant:

1. Upright to somewhat outwardly spreading and mounded plant habit.
2. Moderately vigorous to vigorous growth habit.
3. Dark green-colored leaves.
4. Freely flowering habit.
5. Reddish purple to light purple-colored flowers.
6. Good garden performance.

Plants of the new *Helleborus* differ from plants of the female parent selection in the following characteristics:

1. Leaves of plants of the new *Helleborus* are darker green in color than leaves of plants of the female parent selection.
2. Flowers of plants of the new *Helleborus* are reddish purple to light purple in color whereas flowers of plants of the female parent selection are white in color.

Plants of the new *Helleborus* differ from plants of the male parent selection in the following characteristics:

1. Leaves of plants of the new *Helleborus* are darker green in color than leaves of plants of the male parent selection.
2. Flowers of plants of the new *Helleborus* are reddish purple to light purple in color whereas flowers of plants of the male parent selection are rose pink in color.

Plants of the new *Helleborus* can also be compared to plants of *Helleborus* x *lemperii* 'HGC Lisann', not patented. In side-by-side comparisons, plants of the new *Helleborus* differ primarily from plants of 'HGC Lisann' in flower color as flowers of plants of the new *Helleborus* are reddish purple to light purple in color whereas flowers of plants of 'HGC Lisann' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1012' grown in a container.

Figure 2:
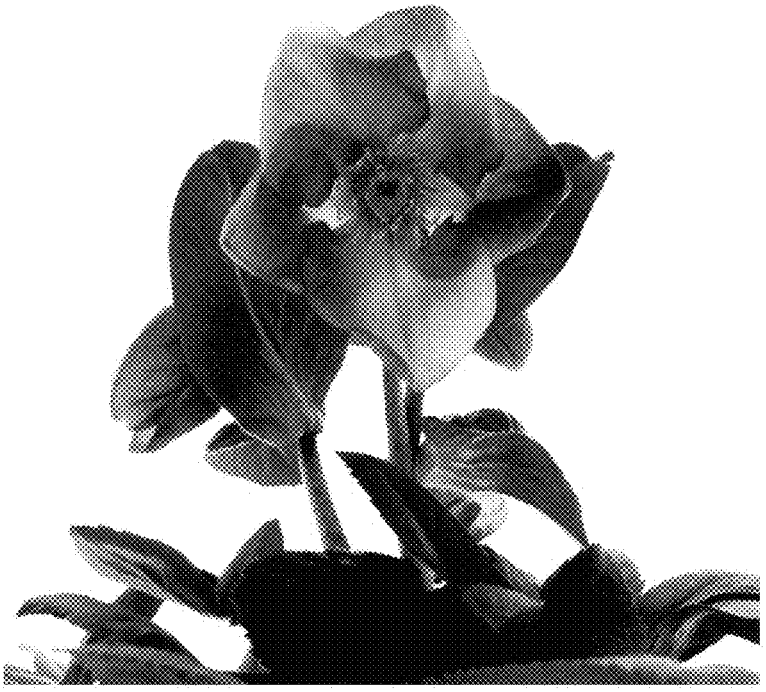

The photograph on the second sheet (FIG. 2) is a close-up view of a typical flowering plant of 'HL 1012'.

DETAILED BOTANICAL DESCRIPTION

The aforementioned photographs and following observations, measurements and values describe plants grown during late autumn and early winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *lemperii* (*Helleborus niger* X *Helleborus* x *hybridus*) 'HL 1012'.

Parentage:

*Female, or seed, parent*.—Proprietary selection of *Helleborus* x *lemperii* identified as code number 2013-0843, not patented.

*Male, or pollen, parent*.—Proprietary selection of *Helleborus* x *lemperii* identified as code number 2013-0684, not patented.

PROPAGATION:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within and above the foliar plane; plant shape, broad inverted triangular; moderately vigorous to vigorous growth habit and moderate growth rate.

*Plant height, soil level to top of foliar plane*.—About 19.2 cm.

*Plant height, soil level to top of flowers*.—About 33.5 cm.

*Plant diameter* (*area of spread*).—About 45.8 cm.

Leaf description:

*Arrangement*.—Leaves arranged in a basal rosette; leaves palmately compound with typically seven leaflets, or occasionally five, per leaf.

*Leaf length*.—About 20.1 cm.

*Leaf width*.—About 23.3 cm.

*Leaflet length*.—About 12.9 cm.

*Leaflet width*.—About 7.3 cm.

*Leaf shape*.—Palmate; roughly reniform in outline.

*Leaflet shape*.—Broadly elliptic to obovate.

*Leaflet apex*.—Acute to broadly acute.

*Leaflet base*.—Attenuate.

*Leaflet margin*.—Serrate; slightly and coarsely undulate.

*Leaflet texture and luster, upper and lower surfaces*.—Smooth, glabrous; moderately coriaceous; slightly glossy.

*Leaflet venation pattern*.—Pinnate.

*Leaflet color*.—Developing leaflets, upper surface: Close to NN137B; towards the base, close to N186C. Developing leaflets, lower surface: Close to 147B. Fully developed leaflets, upper surface: Darker than a blend of NN137A and 147A; towards the base, tinged with close to 200B; venation, close to 144A. Fully developed leaflets, lower surface: Close to 147B; venation, close to 146C.

*Petioles*.—Length: About 15.1 cm. Diameter: About 7.5 mm by 9 mm. Strength: Strong. Texture and luster, upper and lower surfaces: Smooth, glabrous; moderately glossy. Color, upper and lower surfaces: Close to 146C moderately covered with fine dots, close to N186C.

Flower description:

*Flower shape and habit*.—Single rotate bowl-shaped flowers arranged in panicles; freely flowering habit with numerous flowers developing per plant during the flowering season; flowers face mostly outwardly to nodding.

*Fragrance*.—None detected.

*Natural flowering season*.—Plants begin flowering about ten months after planting; plants flower naturally from late full into the winter in Germany.

*Flower longevity on the plant*.—About ten days; sepals persistent, other flower parts are not persistent.

*Flower buds*.—Length: About 3.7 cm. Diameter: About 2 cm. Shape: Elliptic to ovate/oblong. Texture and luster: Smooth, glabrous; matte. Color: Close to a blend of N77B and N77D; towards the base, close to 145C; venation, close to 71A.

*Inflorescence height* (*including peduncle*).—About 33.5 cm.

*Inflorescence diameter*.—About 20 cm.

*Flower diameter*.—About 10.6 cm by 10.6 cm.

*Flower depth*.—About 4 cm.

*Petals*.—All petals are transformed into nectaries.

*Sepals*.—Quantity and arrangement: About five, arranged in a single whorl. Length: About 6.3 cm. Width: About 5.7 cm. Shape: Broadly ovate, slightly concave. Apex: Broadly and bluntly acute to roughly obtuse. Base: Truncate to rounded. Margin: Entire; slightly to moderately undulate. Texture and luster, upper surface: Smooth, glabrous; matte. Texture and luster, lower surface: Smooth, glabrous; matte to slightly glossy. Color: When opening, upper surface: Close to 70A; towards the apex and margins, close to 70B and 75A. When opening, lower surface: Close to 70A; towards the apex and margins, close to 186C to 186D; venation, close to 61A. Fully opened, upper surface: Close to a blend of 70B to 70C and 75A to close to 75C to 75D; towards the apex and margins, occasionally tinged with close to 146D; venation, similar to lamina colors; color does not change with subsequent development. Fully opened, lower surface: Close to 71B and 75B to 75D to close to 186C; towards the apex and margins, occasionally tinged with close to 146C; venation, close to 64A; color does not change with subsequent development.

*Flower bracts*.—Quantity per flower: Typically one or two. Length: About 9.8 cm. Width: About 5.7 cm. Shape: Broadly ovate. Apex: Acute to three-lobed. Base: Truncate to cuneate. Margin: Entire; distally, occasionally sparsely and shallowly serrate; coarsely undulate. Color, upper surface: Close to darker than NN137A; towards the base, tinged with close to 144A. Color, lower surface: Close to a blend of 146B and 147B; venation, close to 146D and proximally, tinged with close to 187A.

*Peduncles*.—Length: About 22.2 cm. Diameter: About 1 cm to 1.1 cm. Aspect: About 10° from vertical. Strength: Strong. Texture and luster: Smooth, glabrous; moderately glossy. Color: Close to a blend of 144B and 146D and heavily covered with fine dots, close to N186C.

*Pedicels*.—Length: About 6.9 cm. Diameter: About 5 mm. Aspect: About 10° from peduncle axis. Strength: Moderately strong. Texture and luster: Smooth, glabrous; moderately glossy. Color: Close to 146D and moderately to heavily covered with fine dots, close to 187A to 187B.

*Reproductive organs*.—Stamens: Quantity per flower: About 100. Filament length: About 1.8 cm. Filament color: Close to NN155D. Anther shape: Double and broadly reniform; basifixed. Anther size: About 2 mm by 3 mm. Anther color: Close to 154C. Pollen amount: Sparse to moderate. Pollen color: Close to 4D. Pistils: Quantity per flower: About six to eight. Pistil length: About 1 cm. Stigma diameter: About 0.3 mm. Stigma shape: Club-shaped. Stigma color: Close to 150D. Style length: About 9 mm. Style color: Close to 64A. Ovary color: Close to 150D; adaxial rib, close to 64A to 64B. Nectaries (transformed petals): Quantity per flower: About 15 to 19. Length: About 1.1 cm. Diameter: About 3 mm. Shape: Tubular, flattened; apices, obtuse. Texture and luster, inner and outer surfaces: Smooth, glabrous; slightly glossy. Color, immature, inner surface: Close to 145A; towards the apex, close to 145C. Color, immature, outer surface: Close to 145B; towards the apex, close to 145C. Color, mature, inner surface: Close to N144D; towards the apex, close to 150C; venation, similar to lamina colors; with subsequent development, color becoming closer to N144B with close to 153D at the apex and at the base, close to 153B. Color, mature, outer surface: Close to N144D; towards the apex, close to 150C; towards the base, close to 152C; venation, similar to lamina colors; with subsequent development, color becoming closer to 152D with close to 153D at the apex and at the base, close to 153B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1012' as illustrated and described.

* * * * *